(12) United States Patent
Meier et al.

(10) Patent No.: US 8,742,094 B2
(45) Date of Patent: Jun. 3, 2014

(54) METHOD FOR THE SOLID PHASE-BASED PRODUCTION OF PHOSPHATE-BRIDGED NUCLEOSIDE CONJUGATES

(75) Inventors: Chris Meier, Jork (DE); Viktoria Caroline Tonn, Hamburg (DE)

(73) Assignee: Universitaet Hamburg, Hamburg (DE)

( * ) Notice: Subject to any disclaimer, the term of this patent is extended or adjusted under 35 U.S.C. 154(b) by 0 days.

(21) Appl. No.: 13/319,108

(22) PCT Filed: May 6, 2010

(86) PCT No.: PCT/DE2010/000508
§ 371 (c)(1),
(2), (4) Date: Jan. 24, 2012

(87) PCT Pub. No.: WO2010/127666
PCT Pub. Date: Nov. 11, 2010

(65) Prior Publication Data
US 2012/0116067 A1    May 10, 2012

(30) Foreign Application Priority Data
May 7, 2009 (DE) .......................... 10 2009 020 261

(51) Int. Cl.
| | |
|---|---|
| *C07H 19/04* | (2006.01) |
| *C07H 19/20* | (2006.01) |
| *C07G 3/00* | (2006.01) |
| *C07H 17/00* | (2006.01) |
| *C08B 37/00* | (2006.01) |
| *C07H 5/04* | (2006.01) |
| *C07H 5/06* | (2006.01) |

(52) U.S. Cl.
USPC ................ 536/26.14; 536/26.216; 536/26.21; 536/18.5; 536/55.3

(58) Field of Classification Search
None
See application file for complete search history.

(56) References Cited

U.S. PATENT DOCUMENTS

2004/0220397 A1* 11/2004 Leuck et al. ................. 536/25.4

OTHER PUBLICATIONS

Pon et al. Bioconjugate Chem. 1999, 10, 1051-1057.*
Napoli, Bioorganic & Medicinal Chemistry 7 (1999) 395-400.*
Tonn, V., Maier, C.: "Solid Phase Synthesis of Nucleoside Diphosphate Glyocpyranoses and Phosphorylated Biomolecules" 15th European Carbohydrate Symposium, PA 067, Jul. 19, 2009-Jul. 24, 2009, p. 249, XP002596654 Vienna, Austria the whole document.
Wendicke, S. et al: "Efficient Synthesis of Nucleoside Diphosphate Glycopyranoses" Angewandte Chemie, vol. 120, Jan. 1, 2008, pp. 15223-1525, XP002554866 2008 Wiley-VCH Verlag GmbH & Co. KGaA, Weinheim, Germany cited in the application, the whole document.
Gaur, R. K. et al: "Novel Solid Phase Synthesis of 2'-O-Methyribonucleoside 5'-Triphosphates and Their Alpha-Thio Analogues" Tetrahedron Letters, Elsevier, Amsterdam, NL LNKD—D01:10:1016/S0040-4039(00)92072-0, vol. 33, No. 23, Jun. 2, 1992, pp. 3301-3304, XP000601548, ISSN: 0040-4039 cited in the application, the whole document.
Parang, K. et al:"Selective diphosphorylation, dithiodiphosphorylation, triphosphorylation, and trithiotriphosphorylation of unprotected carbohydrates and nucleosides" Organic Letters, American Chemical Society, US LNKD—D01:10:1021/0L0521432, vol. 7, Jan. 1, 2005, pp. 5589-5592, XP002464531, ISSN: 1523-7060 cited in the application, the whole document.
Ahmadibeni, Y. et al: "Synthesis of Nucleoside Mono-, Di-, and Triphosphoramidates from Solid-Phase cycloSaligenyl Phosphitylating Reagents" Organic Letters 2009, vol. 11, No. 10, pp. 2157-2160 2009 American Chemical Society.
Pon, Richard T. et al: "Hydroquinone-O, O'Diacetic Acid as a More Labile Replacement for Succinic Acid Linkers in Solid-Phase Oligonucleotide Synthesis" Tetrahedron Letters, vol. 38, No. 19, pp. 3327-3330, 1997 1997 Elsevier Science Ltd., Printed in Great Britain.
Pon, Richard T. et al: "Hydroquinone-O, O'diacetic Acid ('Q-linker') as a replacement for succinyl and oxalyl linker arms in solid phase oligonucleotide synthesis" Nucleic Acids Research, 1997, vol. 25, No. 18, pp. 3629-3625 Department of Medical Biochemistry, The University of Calgary, Calgary, Alberta T2N 4N1, Canada.
Wendicke S.: "Neue Synthese von Nucleosiddiphosphatpyranosen mit Hilfe von cycloSal-aktivierten Phospatdonatoren" Doctoral Thesis, presented to the Department of Chemistry, University of Hamburg, Germany, 2007 English language summary attached.
Tonn, Victoria Caroline "Festphasen-gebundene cycloSal-Nucleotide zur Synthese phosphorylierter Biomoleküle" Dissertation zur Erlangung des naturwissenschaftlichen Doktorgrades von Viktoria Caroline Tonn aus Hildesheim vorgelegt dem Department Chemie der Universität Hamburg—Germany, Hamburg, 2011 English Abstract Attached.

* cited by examiner

Primary Examiner — Layla Bland
(74) Attorney, Agent, or Firm — Patent Central LLC; Stephan A. Pendorf (57) ABSTRACT

The invention relates to a method for producing phosphate-bridged nucleoside conjugates. In the method, a cyclosaligenyl nucleotide is produced first, to which a linker is added, which is used to perform the immobilization on a solid phase. A subsequent reaction with corresponding nucleophiles results in the desired phosphate-bridged nucleoside conjugates, which can then again be cleaved from the solid phase-bound linker.

11 Claims, 2 Drawing Sheets

METHOD FOR THE SOLID PHASE-BASED PRODUCTION OF PHOSPHATE-BRIDGED NUCLEOSIDE CONJUGATES

The invention relates to a method for the solid-phase based production of phosphate-bridged nucleoside conjugates, in particular of nucleoside diphosphate sugars, (poly)phosphorylated nucleosides, dinucleoside polyphosphates and nucleotide sugar conjugates.

Phosphate-bridged nucleoside conjugates are of great importance in nature. They are not only significantly involved in metabolic-energetic processes, but are present in nearly all biosyntheses as metabolites. Dinucleoside-polyphosphates, for example, play an essential role in different biological functions, e.g. as cofactors or as signal and regulator molecules. Nicotineamide adenine dinucleotide (NAD) or flavin adenine dinucleotide (FAD) are, for example, important coenzymes that are essentially involved in cell respiration as hydrogen carriers, and compounds such as the diadenosine tetraphosphate ($Ap_4A$) depicted below $Ap_4A$ as well as related compounds have great diabetic potential. Therefore, the development and production of chemically stable analogues is of great interest in view of the importance of the gluconeogenesis, the glucose uptake, the lipid metabolism and the blood pressure regulation.

Also so-called nucleoside diphosphate or XDP sugars, a special class of carbohydrate derivatives, are of considerable importance. A general formula for such sugars is depicted in the following:

$2\ Kat^+$

Nucl stands for nucleoside, $Kat^+$ for cation. These compounds, also generally designated as sugar nucleotides, consist of a nucleoside bridged via a pyrophosphate unit with a pyranose derivative via the anomeric center. The anomeric phosphate ester groups of the nucleoside diphosphate pyranoses activate the glycosyl residue for enzymatic transfer reactions while the nucleoside residue serves glycosyl transferases or isomerases as additional recognition feature for specific conversions. These activated monosaccharides fulfill two functions essential for the constructive metabolism. They are involved in the biosynthesis of deoxy sugars, of amino deoxy sugars and branched-chain sugars. Further, XDP sugars are the essential building blocks for the biosynthesis of oligosaccharides and the main part of the polysaccharides.

As a further example the naturally occurring ribo- and deoxyribonucleoside triphosphates (NTP's and dNTP's) are to be mentioned. They represent the basic building blocks for the enzymatically catalyzed RNA and DNA synthesis in vivo and in vitro, while their analogs have an enormous potential as inhibitors in many biological processes (e.g. processes in which DNA polymerases are involved) or as chemotherapeutics. For this reason, there is great interest in a synthetic access to these compounds. However, not only the synthesis of nucleoside triphosphates, but, in particular, also their isolation is a big problem. By means of the conversion of highly charged reagents as, for example, pyrophosphate, with lipophilic protected nucleoside derivatives, the manufacture of these compounds is severely hindered on the one hand, whereas, on the other hand, the isolation of a charged water-soluble product from a mixture of hydrophilic and hydrophobic components is very difficult. In addition, nucleoside triphosphates are susceptible for hydrolysis due to their energy-rich anhydride bonds. Their stability depends on both the counter ion and the pH value of the medium (Z. Milewska, H. Panusz, Anal. Biochem. 1974, 57, 8-13).

In the prior art, there are several methods for the preparation of these compounds. The synthetic strategy mostly used for the chemical preparation of nucleoside triphosphates is based on the nucleophilic attack of a pyrophosphate salt on an activated nucleoside monophosphate (M. Yoshikawa, T. Kato, T. Takenishi; Tetrahedron Lett 1967, 50, 5065-68). Pyrophosphate salts as, for example, tris(tetra-n-buylammonium)hydrogenpyrosphate are commercially available, the activated nucleotides, however, have to be synthesized.

The nucleoside phosphorochloridates going back to Yoshikawa et al (supra) were directly converted with bis(tri-n-butylammonium)pyrophosphate by Ludwig (J. Ludwig; Acta. Biochim. et Biophys. Acad. Sci. Hung. 1981, 16, 131-133) and others. The nucleophilic attack of the pyrophosphate ion leads to the formation of the cyclic trimetaphosphate alkyl intermediate (W. Feldmann; Chem. Ber. 1966, 99(10), 3251-3259; A. W. Schwartz; J. Chem. Soc., Chem. Commun. 1969, 1393. Ludwig; Bioact. Mol. 1987, 3, 201-204), which provides the nucleoside triphosphate in the following hydrolysis step.

However, this method is restricted to nucleoside derivatives that are insensitive against the conditions of the monophosphorylation according to M. Yoshikawa, which allows only for a very restricted use of modified purine nucleosides in particular (W. Wu, D. E. Bergstrom, V. J. Davisson, J. Org. Chem. 2003, 68, 3860-3865). Also alkene-functionalized nucleosides, for example, cannot be phosphorylated in this manner, because the HCl formed in the reaction from $P(O)Cl_3$ adds to the alkene function (T. Kovács, L. Ötvös.; Tetrahedron Lett. 1988, 29, 4525-4528). In addition, further problems arise from the lack of selectivity of $P(O)Cl_3$ as phosphorylating reagent (W. H. Dawson, R. L. Cargill, R. B. Dunlap, J. Carbohydr. Nucleosides Nucleotides 1977, 4, 363-375).

Further synthesis pathways for nucleoside triphosphates intensively used in the prior art use nucleoside phosphoromorpholidates (S. Roseman, J. J. Distler, J. G. Moffatt, H. G. Khorana; J. Am. Chem. Soc. 1961, 83, 659-663; J. G. Moffatt, H. G. Khorana; J. Am. Chem. Soc. 1954, 80, 3756-3761.), -amidates (J. Tomasz, A. Simoncsits, M. Kajtar. R. M. Krug, A. Shatkin, J. Nucl. Acids Res. 1978, 5, 2945-2957; A. Simoncsits, J. Tomasz, J. Nucl. Acids Res. 1975, 2, 1223-1233) or -imidazolidates (D. E. Hoard, D. G. Ott, J. Am. Soc. Chem. 1965, 87, 1785-1788; M. Shimazu, K. Shinozuka, H. Sawai, Tetrahedron Lett. M990, 31, 235-238) as activated nucleotides. The conversion to the triphosphate, however, often needs several days and the chemical yields are in many cases rather moderate. In these methods bis(tri-n-butylammonium) pyrophosphate also displaces the morpholine, amine or imidazole residue in a nucleophilic reaction from the 5'-nucleosyl derivative.

A further way of synthesizing nucleoside diphosphate (NDP) sugars is based on the use of activated nucleoside-5'-phosphites or -phosphoramidites. Early works were published by J. W Ludwig and F. Eckstein (J. Ludwig, F. Eckstein, J. Org. Chem. 1989, 54, 631-635), in which nucleosides were converted with a salicylic acid phosphorochloriditeto reactive nucleoside-5'-phosphites, which subsequently reacted in situ at first with bis(tri-n-butylammonium)pyrophosphate to a cyclic intermediate. The subsequent oxidation/hydrolysis then yields the respective triphosphate. An advantage of this synthesis route is the higher reactivity of P(III) reagents. Disadvantageous is, however, the necessary hydrolysis/oxidation step starting from the intermediate.

One way to the synthesis of nucleoside diphosphate (NDP) sugars using so-called cyclosaligenyl(cycloSal) nucleoside phosphate triesters has been described by Wendicke et al. (Angew. Chem. 2008, 120, 1523-1525). These cycloSal-nucleoside phosphate triesters, which are also called cycloSal-NMPs, cycloSal nucleotides or cycloSal triesters, a cyclic phosphate triester derivatives, in which a salicylic alcohol is diesterified in a cyclic manner with a nucleoside monophosphate. The basic structure of the cyclo-saligenyl nucleotides used by Wendicke et al. is depicted in the following.

(IIa)

In the method the cycloSal triester 5-nitro-cycloSal-3'-O-acetyl-thymidinemonophosphate was mixed with respective glycopyranosyl-1-phosphates in anhydrous DMF and a molar ratio of 1:1.2. The resulting NDP sugars where obtained after 3-5 h at room temperature in yields of 40-60%.

A solid-phase based method for the synthesis of nucleoside di- and -triphosphates has been described by Ahmadibeni and Parang (Y. Ahmadibeni; K. Parang; Selective Diphosphorylation, Dithiodiphosphorylation, Triphosphorylation, and Trithiotriphosphorylation of Unprotected Carbohydrates and Nucleosides; Org. Lett. 2005, 7(25), 5589-5592). The synthesis is based on di- and triphosphitylation reagents, which are bound to the solid phase aminomethyl polystyrene. The di- and triphosphitylation reagents initially have to be prepared in threestaged syntheses. After reaction with the desired nucleoside the phospite units are oxidized to phosphate units, i.e. the nucleosides or sugars to be phosphorylated have to be stable under the harsh oxidation conditions (tBuOOH) and under the subsequent cleavage of the cyano groups. After cleavage from the solid phase the raw products were obtained with varying purity and moderate yields. The varying yields show that the method it is not generally applicable to obtain high yields.

Ahmadibeni and Parang also published a method providing nucleoside-5'-O-β-triphosphates (Y. Ahmadibeni; K. Parang; Application of a Solid-Phase β-Triphosphitylating Reagent in the Synthesis of Nucleoside β-Triphosphates; J. Org. Chem. 2006, 71, 5837-5839). However, here also varying purities and moderate yields were obtained. In addition, the method is restricted to a β-phosphorylation.

Von Gaur et al. published a method in which the nucleoside is bound to a solid phase and phosphorylated to the di- or triphosphate (R. K. Gaur, B. S. Sproat; G. Krupp; Novel Solid Phase Synthesis of 2'-O-Methylribonucleoside 5'-triphosphates and their α-thio analogues; Tetrahedron Lett. 1992, 33(23), 3301-3304). The method requires a chromatographic purification at sephadex after the product is cleaved off from the solid phase and provides only moderate yields of 60-65% of the nucleoside-5'-triphosphate. Similar yields shall also be obtainable with the method of Burgess and Cook (K. Burgess; D. Cook; Syntheses of Nucleoside Triphosphates; Chem. Rev. 2000, 100, 2047-2059). Both of the latter methods include the use of the resin CPG (controlled pore glass) as solid phase, which is expensive compared to solid phases based on polystyrene.

Object of the present invention is to provide a method for preparing phosphate-bridged nucleotide bioconjugates, in particular of nucleoside diphosphate sugars, (poly)phosphorylated nucleosides, dinucleoside polyphosphates and nucleoside-sugar conjugates, which is applicable over a wide range and provides the compounds in a manner as simple and rapid as possible and in a yield and purity as high as possible. It is a further object of the invention to provide compounds that can be used in an advantageous manner in the preparation of respective phosphate-bridged nucleotide bioconjugates.

The object is solved by the method and the compounds disclosed in greater detail below.

By "phosphate-bridged nucleoside conjugates" is meant herein compounds of the general formula (I)

or salts thereof, wherein $R^1$ is ONucl or Nucl, and wherein Nucl is a nucleoside or nucleoside analog.

$R^2$ is any organic compound or phosphate or pyrophosphate, or a residue thereof. Preferably, $R^2$ is a compound or a component analogous thereto or a corresponding compound residue which is present in a living cell, for example an alcohol, a sugar, a lipid, a nucleoside, a nucleoside mono-, di- or triphosphate, phosphate or pyrophosphate, or an alcohol, sugar, lipid, nucleoside, nucleoside mono, di- or triphosphate, phosphate or pyrophosphate residue. In this case one also speaks of bioconjugates.

It has surprisingly been found that phosphate-bridged nucleoside conjugates are obtainable in a simple manner in very high yields and purities, when the above outlined "cycloSal" concept is modified in an inventive manner. In the method according to the present invention a compound of the above general formula (I), or a salt thereof, preferably a pharmaceutically acceptable salt thereof, is prepared in that to a compound of the general formula (II)

(II)

a linker (L) is added and a compound of the following formula (III)

(III)

is prepared, and the compound (III) is immobilized to a solid phase containing at least one amino group —NH$_2$, and the immobilized compound (III) is reacted with a nucleophile identical to or comprising R$^2$.

In an alternative embodiment of the method of the invention the linker (L) is already coupled to the solid phase. In this embodiment, the linker (L) being covalently bound to a solid phase is added to the compound according to the general formula (II), and the corresponding reaction product, i.e. the compound (II) coupled to the solid phase via the linker (L), is than reacted with a nucleophile identical to or comprising R$^2$.

R$^1$ and R$^2$ are as defined above. X can be any electron acceptor and is preferably H, OMe, MeSO$_2$, ketone, =O, C=O, COOH, formyl, ester, NO$_2$ or halogen, Me being methyl. In case of a carbonyl group C=O being present in the residue X it is preferred that it is positioned directly at the aromatic ring. The aromatic ring in compound (II) can be one or more times substituted with X, wherein the substituents can be the same or different. The compound according to formula (II) can also be substituted at the C atom 7 (for the numbering see formula IIa), for example with methyl, i-propyl, tert-butyl or other alkyl substituents. As the case may be, also the aromatic ring can have further substituents apart from X, for example alkyl or aryl substituents.

The term "linker" (L) as used herein is understood to mean an organic compound by which the compound (II) and later the compound (I) are covalently bound to the solid phase. The linker preferably has at least two functional groups e.g., oxide groups —COOH, and firstly serves as connecting piece or spacer between the compound (II) and the solid phase, and is covalently connected with both the compound (II) and the solid phase. After reaction with a suitable nucleophile phosphate-bridged nucleoside conjugates according to the present invention are coupled to the solid phase by means of the linker.

A linker preferably used in the present method is, for example, a linker according to the general formula (IV):

(IV)

R$^5$ and R$^6$ being, each independent from each other, H, substituted or unsubstituted alkyl or aryl residues, and n being 1, 2, 3, 4, 5, 6, 7, 8, 9 or 10. "Independent from each other" in relation to R$^5$ and R$^6$ shall also mean that in case of n>1 multiple residues R$^5$ and multiple residues R$^6$ may be independently from each other H, substituted or unsubstituted alkyl or aryl residues, so that the first residue R$^{5(1)}$ may, for example, be H, and a further residue may, for example, be methyl. The covalent bond is in this case realized via the two carboxyl groups.

However, also other linkers may be employed in the method of the invention, for example benzoyl linkers, e.g. having the structure —OC—C$_6$H$_4$—O— or —OC—C$_6$H$_4$—. Such benzoyl linkers can, for example, be reacted with the compound (II) in the form of the corresponding carboxylic acid halide (e.g. carboxylic acid chloride). Linkers are generally known to the person skilled in the art and he or she will, after routine experimentation if need be, choose the linker suitable for the given purpose.

In this context, it is understood by one skilled in the art that the OH groups of the carboxyl groups of the linker (IV) are cleaved off during the addition to the compound (III) and the binding to the solid phase and that the term linker also comprises the corresponding residue, for example according to the general formula (IVa)

(IVa)

The same applies, of course, in case of the benzoyl linkers. Here also, the term comprises both the bound residue and the "free" compound or the compound only coupled to the solid phase.

The term "succinyl linker" as used herein means a compound according to the general formula (IVb)

(IVb)

or a corresponding residue (see above). A succinyl linker can, for example, be added to the compound (II) by reacting succinic anhydride with compound (II).

A great advantage of the method according to the invention is its broad applicability to a wide variety of compounds. With the method of the invention any phosphate-bridged nucleoside conjugate can be prepared with high yield and purity, for example nucleoside diphosphate glycopyranoses. Using phosphate and pyrophosphate salts, for example, nucleoside di- and nucleoside triphosphates can be prepared. With the method according to the invention, also nucleoside analogs can be prepared in an advantageous manner, which may for example be employed as "prodrugs". "Prodrugs" are precursors of active agents releasing the active agent later under cleaving off of masking groups.

Further, besides dinucleoside monophosphates also dinucleoside polyphosphates according to the general formula (V)

abbreviated Np$_n$N' can be prepared. N and N' stand here for nucleoside or nucleoside analog, N and N' being the same or different. P stands for phosphate, the index n represents the number of the linked phosphate residues and is preferably 2, 3 or 4. An example for a dinucleoside polyphosphate is the diadenosine tetraphosphate (Ap$_4$A) already mentioned above. Also NAD or FAD are dinucleoside polyphosphates in the sense of the present invention.

In addition, it is also possible to prepare sugar-nucleoside bioconjugates by means of the method according to the invention.

"Organic compounds" are all compounds having bonds of carbon with carbon and with other elements (with the exception of carbon dioxide, carbon monoxide, carbonic acid and its carbonates, and cyanides, isocyanides, cyanates and isocyanates of metals). Examples for organic compounds are carbohydrates, i.e. compounds of carbon and hydrogen, alcohols, aldehydes, ketones, carboxylic acids, amines, amides, nitro compounds, nitriles, alkanethiols, sulfides, sulfates, phosphates, phosphines, metalorganic compounds, aliphatic hydrocarbons, acyclic hydrocarbons, saturated (alkanes), unsaturated (alkenes and alkines), cyclic hydrocarbons, mono- or polycyclic aromatic hydrocarbons (aromatics), heterocycles, biochemical compounds (amino acids, proteins, nucleoside is, nucleotides, hydrocarbons, lipids) etc.

Under the term "carbocycle" cyclic compounds are to be understood of which the ring-forming atoms consist exclusively of C atoms.

A "heterocycle" is a cyclic compound with ring-forming atoms of at least two different chemical elements. In particular, the term means a ring-forming organic component in which ring structure at least one carbon atom is replaced by another element, i.e. a heteroatom, for example nitrogen, oxygen and/or sulfur. A ring structure can consist of one or more rings connected with each other and may contain one or more identical or different heteroatoms.

The term "nucleophile" is known to the skilled person and has the meaning familiar to the skilled person. In particular, as used herein, a nucleophile means a molecule containing a negatively polarized region, a negatively polarized functional group or a free electron pair, generally in an energy rich orbital. The term also covers molecules being nucleophile, i.e. relatively electron richer in relation to a reaction partner or to a region of the reaction partner. The reaction partner also is termed electrophile, because it assumes electrons from the nucleophile. Nucleophiles may form covalent bonds by providing electrons to a reaction partner. The electrons necessary for the bond are generally from the nucleophile alone. Nucleophiles can be negatively charged (anions). Examples for typical nucleophile reagents are carbanions, anions, Lewis bases, aromatics, alcohols, amines, e.g. amino acids, and compounds with olefinic double bonds.

The strength of the nucleophilicity depends, for example, on the reaction partner, the basicity, the solvent and sterical factors. The factors affecting the nucleophilicity of a compound are well known to the skilled person, and he can easily determine their nucleophilic properties. The nucleophilicity of a molecule will advantageously be related to the most nucleophilic atom or the most nucleophilic functional group.

In case the cycloSal phosphate triesters according to the above general formula (II) are employed as electrophile the electrophilicity of the phosphorus atom can be controlled via the substituent X at the cycloSal aromatic ring (S. C. Meier, J. Renze, C. Ducho, J. Balzarini, Curr. Topics in Med. Chem. 2002, 2, 1111-1121, the disclosure of which is incorporated herein by reference in its entirety). By the introduction of donor substituents at the aromatic ring the electrophilicity can be reduced, acceptor substituents, however, increase the reaction rate of the initial reaction, i.e. the cycloSal ring opening.

An "electron acceptor" is a compound, a region of a compound or a functional group, drawing electrons to it and thereby causing a charge displacement, i.e. a polarization, in a compound. Examples of electron acceptor groups are OMe, MeSO$_2$, =O, COOH, ketones or the keto group, formyl, esters or the ester group, NO$_2$ and halogen (e.g. F, Cl, Br, I). Me represents methyl. Preferred esters as electron acceptors are esters whose ester group is situated as close as possible to, preferably directly at the aromatic ring. Ketones preferred as electron acceptors are ketones whose keto group is situated as close as possible to, preferably directly at the aromatic ring.

Esters are compounds containing the ester group R'—COO—R", wherein R' and R" may be any substituted or unsubstituted, branch- or straight-chained hydrocarbon residues, for example alkyl residues or aryl residues.

Ketones are compounds containing the keto group R'—CO—R", wherein R' and R" are any substituted or unsubstituted, branch- or straight-chained hydrocarbon residues, for example alkyl residues or aryl residues.

By "nucleoside" is meant herein organic molecules consisting of a sugar residue (sugar component) and an organic base (base component), e.g. a heterocyclic organic base, in particular a nitrogen containing heterocyclic organic base, being connected via a glycosidic bond. The sugar residue often is a pentose, e.g. deoxyribose or ribose, but may also be another sugar, e.g. a C$_3$, C$_4$ or C$_6$ sugar. In particular, by nucleoside is meant a compound according to the general wherein B is a nitrogen containing heterocyclic base, e.g. a nucleobase, and R$^3$ and R$^4$ are, independent from each other, H or OH.

By "nucleobase" is meant organic bases occurring in RNA or DNA. Nucleobases are often purines (R) and pyrimidines (Y). Examples for purines are guanine (G) and adenine (A), examples for pyrimidines are cytosine (C), thymine (T) and uracil (U). Phosphorylated nucleoside, for example nucleoside monophosphate (NMP), nucleoside diphosphate (NDP) and nucleoside triphosphate (NTP) are also termed nucleotides. The phosphate, diphosphate (pyrophosphate) or triphosphate group is generally connected with the 5'-C-atom of the sugar component of the nucleoside, but can, for example, also be connected with the 3'-C-atom.

By "nucleoside analog" is meant herein a compound, which naturally does not occur in the human body, but is structurally similar to a nucleoside naturally occurring in the human body, such that it can be processed by the cell and/or by viral enzymes essentially analogous to the natural nucleoside, for example phosphorylated and incorporated into an RNA or DNA strand. A nucleoside analog can itself be a nucleoside. It can, however, for example also be another compound with the above properties, for example a compound of a heterocyclic base and an acyclic residue and/or a residue that is not a sugar, or a compound of a carbocyclic compound and a sugar residue. Nucleoside analogs are either itself nucleosides in the above sense or structurally and/or functionally analogous to nucleosides. Since the nucleoside analogs may not necessarily contain a sugar or base component in a narrower sense, it is also spoken of a component analogous to the base component (base analog) or a component analogous to a sugar component (sugar analog). In case a sugar component or a base component is mentioned here the corresponding analogous components of nucleoside analogs shall also be encompassed, unless the context unambiguously requires otherwise. Examples for nucleoside analogs are, for example, AZT (3'-azido-2',3'-dideoxythimidine, azidothymidine), 2',3'-dideoxyinosine (didanosine), 2',3'-didesoxycytidine (zalticabine) and 2-amino-9-((2-hydroxyethoxy)methyl)-1H-purine-6(9H)-one (acyclovir). Nucleoside phosphonates can also be nucleoside analogs.

By the term "glycosyl phosphate" is meant a phosphorylated glycosyl residue. A "glycosyl" is a compound with a functional group derived from a sugar by elimination of hemiacetal hydroxyl group. Examples for glycosyl-1-phosphates are: glucose-1-phosphate, mannose-1-phosphate, galactose-1-phosphate, 2-N-acetyl-glucosamine-1-phosphate, 6-deoxygulose-1-phosphate, 2-N-acetyl-galactosamine-1-phosphate, D-fucose-1-phosphate and L-fucose-1-phosphate; each in the α or β configuration at the anomeric center (in case of mannose there is only the α form).

The term "alkyl" includes saturated aliphatic groups, including straight-chained alkyl groups (e.g. methyl, ethyl, propyl, butyl, pentyl, hexyl, heptyl and octyl), branch-chained alkyl groups (e.g. isopropyl, tert-butyl, isobutyl), cycloalkyl (e.g. alicyclic) groups (e.g. cyclopropyl, cyclopentyl, cyclohexyl, cycloheptyl, cyclooctyl), alkyl-substituted cycloalkyl groups and cycloalkyl-substituted alkyl groups. "Alkyl" further includes alkyl groups having oxygen, nitrogen, sulfur or phosphor atoms replacing one or more carbon atoms of the hydrocarbon backbone. The term also comprises O, N, S or P alkyl groups (e.g. —O-methyl), i.e. alkyl groups bound via oxygen, nitrogen, sulfur or phosphor atom to a compound. The term "alkyl" also includes un-substituted alkyls as well as substituted alkyls, the latter referring to alkyl residues having substituents replacing the hydrogen atom at one or more carbon atoms of the hydrocarbon backbone. Such substituents may, for example, include: alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, aialkylaminocarbonyl, alkylthiocarbonyl, alkoxyl, phosphate, phosphonato, phosphinato, cyano, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, alkylsulfinyl, sulfonato, sulfamoyl, sulfonamide, nitro, trifluoromethyl, cyano, azido, heterocyclyl, alkylaryl or an aromatic or heteroaromatic residue. Cycloalkyls can be further substituted, e.g. with the above-mentioned substituents. An "alkylaryl" or "aralkyl" residue is an alkyl substituted with an aryl (e.g. phenylmethyl (benzyl)). "Alkyl" also includes the side chains of natural and unnatural amino acids.

By "aryl" is meant groups with aromaticity, including 5- and 6-membered aromatic single-ring groups, which may contain zero to four heteroatoms, and multi-cyclic systems with at least one aromatic ring. Examples for aryl groups include benzene, phenyl, furan, thiophene, thiazole, isothiazole, imidazole, triazole, tetrazole, pyrazole, oxazole, isooxazole, pyridine, pyrazine, pyridazine and pyrimidine, and such like. Further, the term "aryl" includes multi-cyclic aryl groups, e.g. tricyclic and bicyclic, e.g. naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine or indolizine. Under "aryl" also aryl groups are understood, which have heteroatoms in the ring structure ("heteroaryls"). The aromatic ring may be substituted at one or more ring positions. Aryl groups may also be fused or bridged with alicyclic or heterocyclic rings, which are not aromatic, such that a multi-cyclic system is formed (e.g. tetraline, methylenedioxyphenyl). The term also encompasses O, N, S, or P aryl groups, i.e. aryl groups bound via an oxygen, nitrogen, sulfur or phosphor atom to a compound.

By "amine" is meant compounds of the type R—NH$_2$, NH—R$_2$, N—R$_3$ and N—R$_4^+$, R representing a substituted or unsubstituted alkyl or aryl residue, wherein, in case of multiple residues, these can be different or the same. The residues may be closed to a ring, so that the term also encompasses cyclic amines.

By the term "protecting group" as used herein is meant a molecule or molecule residue, which blocks a functional group within a compound during a reaction at another site of the compound and which prevents unwanted (side) reactions. A protecting group can ideally be introduced under the mildest conditions possible, is stable under the subsequent conditions, and can mildly be cleaved off after the reaction. Protecting groups are well known to the skilled person, so that he or she will easily find a suitable protecting group, if necessary, after routine experimentation. Examples for a protecting group are the methyl, acetyl and benzoyl group. For example, an OH group can be protected against its conversion by O methylation or O acetylation.

In a preferred embodiment of the method of the invention a linker (L) according to the general formula (IV)

(IV)

is used in step a) and a compound of the general formula (IIIa)

(IIIa)

is produced, wherein R$^5$ and R$^6$ are, each independent from each other, H, substituted or unsubstituted alkyl or aryl residues, and n is 1, 2, 3, 4, 5, 6, 7, 8, 9 or 10.

In the linker (IV) n is preferably 2, and R$^5$ and R$^6$ are both H, so that the linker has the structure HOOC—(CH$_2$)$_2$—COOH or —OC—(CH$_2$)$_2$—CO—. In this case also the term succinyl linker is used.

In one embodiment the linker is preferably covalently bound to an OH group of the sugar component of the nucleoside or to a component analogous to a sugar component of the nucleoside analog of R'. In case of a pentose this may e.g. be an OH group at the 2'- or 3'-C-atom. Basically, however, also OH groups at other sites of the nucleoside or nucleoside analog are a possibility. OH groups or, as the case may be, other functional groups at which no reaction shall take place can be protected with a protecting group.

Alternatively or also additionally the linker (L) can be attached to the base component or, in case of nucleoside analogs, at the component analogous thereto. For example, the linker can be covalently bound to a nitrogen atom of the base component of the nucleoside or to a component analogous to the nucleoside analog of R'. In case of a linker at the base component or the base analog preferably a benzoyl linker, e.g. of the formula —OC—C$_6$H$_4$—, is used, in which case the attachment to R' preferably occurs via the functional group —OC—. This can, for example, occur by means of a corresponding acid chloride, as depicted below:

In a preferred embodiment the nucleoside or the nucleoside analog is a pentose, and the linker, being a succinyl linker here, is covalently bound to the 3'-position of the pentose. In such a case a compound of the following general formula (IIIb)

is preferably used as compound (III), B being a heterocycle, preferably a nitrogen-containing heterocycle, and R$^3$ being H, OH or a protecting group (PG).

In a preferred embodiment B is one of the nucleobases guanine, adenine, cytosine, thymine or uracil. However, B can, for example, also be a nucleobase analog.

For use as a solid phase any solid phases, i.e. compounds being essentially insoluble under the conditions chosen, come into consideration. Preferred solid phases have at least one free amino group —NH$_2$, preferably a plurality of free amino groups. This is, however, e.g. in case of a benzoyl linker, not necessarily required. In an especially preferred embodiment of the method of the invention the solid phase is a polystyrene (PS). A solid phase having amino groups is, for example, aminomethyl polystyrene (AMPS).

The nucleophile is preferably selected from the group consisting of phosphate, pyrophosphate, glycosylphosphate, nucleoside, nucleoside monophosphate, nucleoside diphosphate, nucleoside triphosphate, nucleoside analog, nucleoside monophosphate analog, nucleoside diphosphate analog, nucleoside triphosphate analog, and α-deprotonated glycosyl, amines, amino acids, or salts, preferably pharmaceutically acceptable salts thereof.

For example, in case of phosphate nucleoside diphosphates, in case of pyrophosphate nucleoside triphosphates can be prepared, compounds of great importance. The use of glycosyl phosphates leads to XDP sugars, an also very important class of compounds.

Dinucleoside polyphosphates according to the above formula (V) are yielded as a product from the use of nucleoside mono-, -di- and -triphosphates as nucleophile. Dinucleotides like NAD or FAD can be prepared in that the corresponding nucleoside monophosphates are used as nucleophile. Compounds like diadenosine tetraphosphate can be prepared by using adenosine triphosphate (ATP). Besides a 5'-5'-linkage of the nucleosides also a 5'-3'- or a 3'-3'-bridging is, for example, possible. For this, only the educts used have to be selected accordingly.

The usage of, for example, α-deprotonated glycosyl as nucleophile leads to sugar-nucleotide-bioconjugates.

In an especially preferred embodiment of the method of the invention the nucleoside of compound (II) is selected from the group consisting of adenosine, guanosine, cytidine, thymidine, uridine, deoxyadenosine, deoxyguanosine, inosine, deoxycytidine, deoxyuridine, deoxythymidine, 2-thiocytidine, N$^4$-acetyl-cytidine, 2'-o-methyl-cytidine, 3-methyl-cytidine, 5-methyl-cytidine, 2-thiouridine, pseudouridine, dihydrouridine, 5-(carboxyhydroxymethyl)uridine, 5-carboxymethylaminomethyl-uridine, 5-methylaminomethyl-uridine, 5-methoxy-carbonylmethyl-uridine, 5-methoxy-uridine, ribothymidine, 1-methyl-adenosine, 2-methyl-adenosine, N$^6$-methyl-adenosine, inosine, 1-methyl-inosine, guanosine, N$^2$-2,2-dimethyl-guanosine, N$^2$-2-methyl-guanosine, 7$^+$-methyl-guanosine, 2'-O-methyl-guanosine.

Nucleosides or nucleoside analogs and nucleoside mono-, -di- and -triphosphates or mono-, di- and triphosphates of nucleoside analogs can be used both in the compound according to formula (II) and in the nucleophile or as a nucleophile. One of the nucleosides mentioned above for compound (II) can, for example, be a nucleoside used as a nucleophile. In case a nucleophile-nucleoside or nucleophile-nucleoside-analog, i.e. a nucleoside or nucleoside analog or their phosphates provided for as a nucleophile, is used, the nucleoside in compound (II) and the nucleophile-nucleoside can be the same or different, are, however, preferably different.

In a preferred embodiment of the method of the invention the linker is cleaved from R$^1$. In this manner, the conjugate according to the general formula (I) is released, if necessary after suitable purification steps. The cleavage of the linker can, for example, be brought about by exposure to NH$_3$, e.g. in form of a NH$_3$ solution.

Especially preferred, the method is carried out under a suitable inert gas, for example nitrogen gas.

In a further aspect, the invention also relates to a compound according to the general formula (IIIa)

wherein the compound (Ma) may be substituted one or more times with X,

X is an electron acceptor, $R^1$ is ONucl or Nucl, wherein Nucl stands for nucleoside or nucleoside analog, n is 1, 2, 3, 4, 5, 6, 7, 8, 9 or 10 and $R^5$ and $R^6$ are, each independent from each other, H, substituted or unsubstituted alkyl or aryl residues.

Preferably, the compound of the invention is a compound of the general formula (IIIb)

(IIIb)

wherein B is a heterocycle, preferably a nitrogen-containing heterocycle, and $R^3$ is H, OH or a protecting group.

X is, in case of multiple substituents X independently from each other, selected from the group consisting of H, Me, OMe, MeSO$_2$, ketone, formyl, ester, =O, C=O, COOH, NO$_2$ and halogen.

Preferably, B is one of the nucleobases guanine, adenine, cytosine, thymine or uracil. B can, however, also be a nucleobase analog.

Nucl is preferably selected from the group consisting of adenosine, guanosine, cytidine, thymidine, uridine, deoxyadenosine, deoxyguanosine, inosine, deoxycytidine, deoxyuridine, deoxythymidine, 2-thiocytidine, $N^4$-acetyl-cytidine, 2'-O-methyl-cytidine, 3-methyl-cytidine, 5-methyl-cytidine, 2-thiouridine, pseudouridine, dihydrouridine, 5-(carboxyhydroxymethyl)uridine, 5-carboxymethylaminomethyl-uridine, 5-methylaminomethyl-uridine, 5-methoxy-carbonylmethyl-u of uridine, 5-methoxy-uridine, ribo-thymidine, 1-methyl-adenosine, 2-methyl-adenosine, $N^6$-methyl-adenosine, inosine, 1-methyl-inosine, guanosine, $N^2$-2,2-dimethyl-guanosine, $N^2$-2-methyl-guanosine, $7^+$-methyl-guanosine and 2'-O-methyl-guanosine.

In the following, the invention is described in more detail by means of an example and FIGS. 1 and 2.

FIG. 2A shows a general structure, FIG. 2B a corresponding thymidine derivative. PS=polystyrene FIG. 1 illustrates schematically a preferred embodiment of an alternative of the method of the invention. Initially, in step (a1) a cycloSal nucleotide is reacted with succinic anhydride, whereby a compound according to formula IIIb is formed. An OH group possibly present at the pentose, e.g. ribose, at the 2' Position is preferably protected with a protecting group. The method step adds a succinyl linker according to formula (IV) to the 3'-C-atom of the pentose. In the following step (a2) the linker is covalently coupled with the aminomethyl polystyrene (AMPS) solid phase. Subsequently, the linker is bound via an amide bond to the solid phase AMPS. In the following step (c) the attack of the nucleophile (Nu) used on the phosphor atom of the cycloSal phosphate triester occurs. The phenyl phosphate ester bond of the cycloSal compound is dissolved and the nucleophile forms a covalent bond with the phosphor atom. Subsequently, the conjugate composed of the nucleotide and the nucleophile by a spontaneous reaction. In a further step (d) the conjugate formed is cleaved from the linker, e.g. by using NH$_3$.

Figure 1:
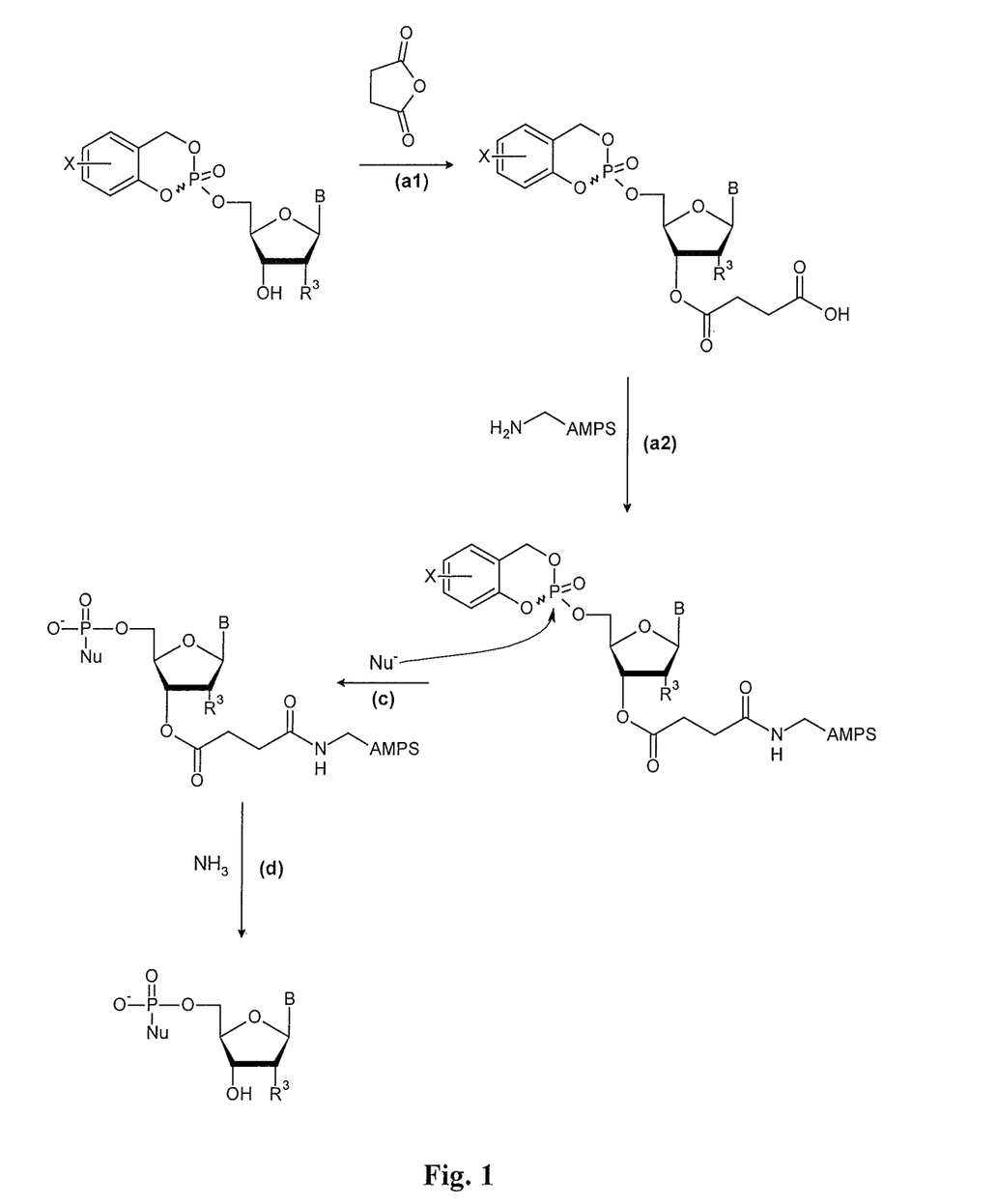
FIG. 1 Schematic depiction of a preferred embodiment of the method of the invention.
Figure 2:
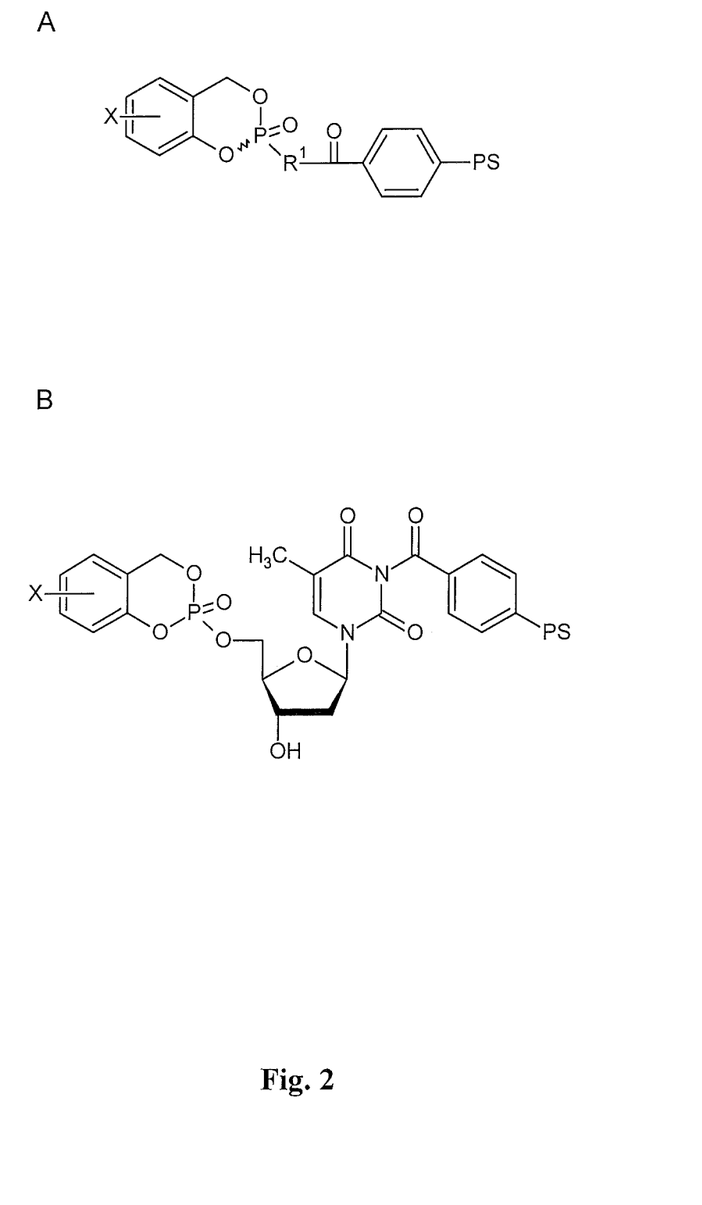
FIG. 2 Exemplary illustration of compounds (II) coupled to the solid phase via a benzoyl linker.

In the example compounds (II) shown in FIG. 2 bound to a solid-phase AMPS is not used as solid phase but polystyrene (PS). The benzoyl linker(s) is (are) bound to the polystyrene.

The examples described below show that it is possible with the method of the invention to synthesize phosphate-bridged nucleoside conjugates, in particular nucleoside di- and -triphosphates, nucleoside diphosphate sugars and diphosphate-bridged nucleosides, in high purity of 77-91% relative to the immobilized cycloSal phosphate triester. A marked advantage compared to the synthesis of these compounds in solution is, for example, the possibility to employ reagents in great excess and thus to achieve high yields. In addition, it is also possible by means of this method to prepare large amounts of a desired product, because the chromatographic separation of the polar reagents, which is problematic in solution, is omitted. The method of the invention is applicable to a wide variety of compounds and opens new ways for the preparation of many target molecules.

EXAMPLE 1

Preparation of Nucleoside Diphosphates

At first, the preparation of nucleoside diphosphates is described using the example of thymidine phosphate 1.1 Anchoring of a Cyclosal Phosphate Triester with a Base-Cleavable Linker The reaction is carried out under nitrogen as inert gas. A 5-chloro cycloSal phosphate triester of thymidine 11 synthesized according to an established method (C. Meier; cycloSal Phosphates as Chemical Trojan Horses for Intracellular Nucleotide and Glycosylmonophosphate Delivery—Chemistry Meets Biology; Eur. J. Org. Chem. 2006, 1081-1102) is combined with 1.5 eq. of succinic acid anhydride and coevaporated twice with abs. acetonitrile. The reagents are dissolved in abs. dichloromethane and supplemented with 1 eq. of diazabicycloundecene (DBU). After complete conversion of the triester (20-40 min) 2 eq. of acetic acid are added to the reaction mixture and stirred for 10 min. Then extraction with dist. water and dichloromethane follows, the organic phases are combined, dried over sodium sulfate, and the solvent is removed under reduced pressure. The residue is purified at the chromatotron with dichloromethane and a methanol gradient (+0.1% acetic acid). The reaction proceeds quantitatively, but the separation of the sole residue, excess of succinic acid anhydride, at the chromatotron leads to an isolated yield of 12 of 75%.

12

1.2 Solid Phase Reaction

All reactions at the insoluble solid phase aminomethyl polystyrene 13 (AMPS, 1.1 mmol/g, 100-200 mesh, copolymer of styrene and 1% divinylbenzene)

aminomethyl polystyrene (AMPS)

X = CH₂NH₂;
Ph = phenyl are performed in a frit and under nitrogen as inert gas. Before a reaction, the resin is dried in vacuum and, if necessary for the reaction, coevaporated. Then the resin is swollen in abs. DMF for half an hour (approx. 1 mL per 0.1 mmol loading) in order to enable a better penetration of the reagents into the solid-phase matrix. The reactions are agitated on a shaker. The washing procedures are also performed under nitrogen. The solvents used do not need to be absolutely pure. The cleavage from the resin is accomplished with 25% aqueous NH₃ solution for 2 h at 50° C. The cleaving solution is removed and the resin washed four times with a total of 50 mL H₂O. Washing and cleaving solution are combined and freeze-dried. The nucleoside immobilized at the solid phase, the amount of which is known because of the Kaiser test (see below), is cleaved off quantitatively during the two-hour cleavage reaction. The purities mentioned in the following passages relate to those raw products. If the nucleoside 5'-monophosphate formed as a side product due to incomplete conversion of the cycloSal phosphate triester is present in the residue this can be removed by subsequent RP18 chromatography.

1.3 Immobilization of Cyclosal Phosphate Triesters at the Solid Phase

The immobilization of the cycloSal phosphate triesters 12 is based on an amide bond between the amino group (=anchor group) of the resin aminomethyl polystyrene (AMPS) 13 and the carboxylic acid group of the linker. This is stable during all further conversions, and the linker remains at the resin after cleavage. For the coupling, a linker-bound 5-chloro-cycloSal phosphate triester 12 is dissolved with equimolar amounts of N,N'-diisopropylcarbodiimide (DIC) and 1-hydroxybenzotriazole (HOBt) in absolute DMF. This solution is added to 0.75 eq. of resin aminomethyl polystyrene 13 swollen in DMF and shaken at room temperature. The reaction time is at least 2 days. The reaction is stopped when all amino groups of the resin are occupied. This is controlled by means of the Kaiser test, which is based on the reaction on ninhydrin with free primary amino groups (V. K. Sarin, S. B. H. Kent; J. P. Tam, R. B. Merrifield; Quantitative monitoring of solid-phase peptide synthesis by the ninhydrin reaction; Anal. Biochem. 1981, 117, 147-157).

Under the same coupling conditions also the immobilization of the 5-chloro cycloSal phosphate triesters of BVdU 14 ((E)-5-(2-bromovinyl)-2'-deoxyuridine, Brivudine, Zostex®) was carried out.

12: R = CH₃
14: R = CHCHBr

15: R = CH₃
16: R = CHCHBr

1.4 Solid-Phase Synthesis of Nucleoside-5' Polyphosphates

For the thymidine diphosphate synthesis the phosphate used as nucleophile is initially synthesized in its tetra-n-butylammonium form by titrating phosphorus acid with tetra-nbutylammoniumhydroxide to a pH value of 5. 6 equivalents of the phosphate obtained as a hygroscopic salt after freeze-drying are dried in a nitrogen atmosphere in absolute DMF over molecular sieve 4 Å for at least 3 h. The resin 15 loaded with cycloSal phosphate triester is coevaporated in a frit three times with abs. MeCN and swollen in abs. DMF. Subsequently, the phosphate is added to the resin and shaken for 16 h at RT. After removal of the reaction solution the resin is washed four times each with a total of 50 mL of each of DMF, DCM and H₂O and subsequently dried for 0.5 h in an oil pump vacuum. After quantitative cleavage and freeze-drying the thymidine-5'-diphosphat 17 is obtained with a purity of 90% in relation to the cycloSal phosphate triester immobilized at the solid phase.

BVdU-5'-diphosphate 18 was prepared in an analogous manner using 16 eq. of the phosphate salt and obtaining a purity of 91%.

15: R = CH₃
16: R = CHCHBr

17: R = CH₃
18: R = CHCHBr

EXAMPLE 2

Preparation of Nucleoside Triphosphates

Syntheses of the nucleoside-5'-triphosphates of thymidine, 19, and BVdU, 20, were carried out analogous to the nucleoside-5'-diphosphates with pyrophosphate as nucleophile in the tetra-n-butylammonium form and a pH value of the salt of approximately 5. 4 equivalents of the salt were used in the case of thymidine, and 34 eq. in the case of BVdU, and a purity, in relation to the cycloSal phosphate triester immobilized at the solid phase, of 89% for 19 and 93% for 20 was achieved. Such an extremely high excess of nucleophile as used in the case of the BVdU is not necessarily required. It was employed here, because BVdU is very expensive and a correspondingly high yield was expected by using the high excess. 4 equivalents pyrophosphate are, however, usually sufficient for a high yield of nucleoside-5'-diphosphate.

15: R = CH₃
16: R = CHCHBr

19: R = CH₃
20: R = CHCHBr

EXAMPLE 3

Solid-Phase Synthesis of Dinucleoside-5'-Polyphosphates

At first, the uridine-5'-monophosphate used as nucleophile is converted via ion exchange (Dowex 50X8) from the disodium into the tetra-n-butylammonium form with a pH value of the salt of approximately 5. 8 equivalents of the UMP obtained as a hygroscopic salt after freeze-drying are dried in a nitrogen atmosphere in absolute DMF over molecular sieve 4 Å for at least 3 h. The resin 15 loaded with cycloSal phosphate triester is coevaporated in a frit three times with abs. MeCN and swollen in abs. DMF. Subsequently, UMP and some grains of activated molecular sieve 4 Å are added to the resin and shaken for 5 d at RT. After removal of the reaction solution the resin is washed four times each with a total of 50 mL of each of DMF, DCM and H₂O and subsequently dried for 0.5 h in an oil pump vacuum. After quantitative cleavage and freeze-drying UP₂T 21 is obtained with a purity of 77% in relation to the cycloSal phosphate triester 15 immobilized at the solid phase.

21

EXAMPLE 4

Solid-Phase Synthesis of Nucleoside-5'-Diphosphate Sugars

The peracetylated β-D-glucopyranosyl-1-phosphate used as nucleophile is obtained as triethylammonium salt according to an established method (J. W. Perich, R. B. Johns; A New Convenient and Efficient General Procedure for the Conversion of Alcohols into their Dibenzyl Phosphoramidite; Tetrahedron Lett. 1987, 28, 101-102). This is converted via ion exchange (Dowex 50X8) into the tetra-n-butylammonium form with a pH value of the salt of approximately 5 and freeze-dried. 9 equivalents of the salt obtained are dried in an oil pump vacuum and dried in absolute DMF over molecular sieve 4 Å for 6 h. The resin 15 is coevaporated in a frit three times with abs. MeCN and swollen in abs. DMF. Subsequently, the sugar phosphate is added to the resin and shaken for 6 d at RT. After removal of the reaction solution the resin is washed four times each in a nitrogen atmosphere with a total of 200 mL DMF and 40 mL DCM in each case and subsequently dried for 0.5 h in an oil pump vacuum. After cleavage and freeze-drying deacetylated thymidine-5'-diphosphate-β-D-glucopyranose 22 is obtained with a purity of 78% in relation to the cycloSal phosphate triester 15 immobilized at the solid phase. Chromatographic purification at RP18 silica gel enables the removal of nucleoside-5'-monophosphate formed to 16% as a side product and the remaining 6% of impurities. The sugar phosphate used in excess can be retrieved by regeneration of the reaction solution. For this purpose, the solution is freed from the solvent and the residue is chromatographed (MeCN/H$_2$O 7:3).

The invention claimed is:
1. A method for the solid-phase based production of a compound of the general formula (I):

or a salt thereof, wherein
    R$^1$ is ONucl or Nucl, wherein Nucl is a nucleoside selected from the group consisting of adenosine, guanosine, cytidine, thymidine, uridine, deoxyadenosine, deoxyguanosine, deoxycytidine, deoxyuridine, and deoxythymidine, or an analog thereof,
    R$^2$ is an organic compound or phosphate or pyrophosphate,
comprising the steps of:
    a) adding a succinyl linker (L) HOOC—(CH$_2$)$_2$—COOH or —OC—(CH$_2$)$_2$—CO— to a compound of the general formula (II)

wherein R$^1$ is as defined above and the compound (II) may be substituted one or more times with X, X being an

15

1. 9.7 eq. Ac$_4$GluPO$_4$HNBu$_4$
   DMF, 6 d, RT, [N$_2$]
2. NH$_3$, 2 h, 50° C.

22 electron acceptor, and where the succinyl linker (L) is covalently bonded to an OH group of the sugar component of the nucleoside of $R^1$ or to a component analogous to a sugar component of the nucleoside analog of $R^1$, for the production of a compound of the formula (III)

wherein X and $R^1$ are as defined above and L=linker, and immobilizing the compound (III) by covalently binding the linker (L) to a solid phase having at least one amino group —$NH_2$, or b) covalently binding a succinyl linker HOOC—$(CH_2)_2$—COOH or —OC—$(CH_2)_2$—CO—, which has been covalently bound to a solid phase, to the compound according to the general formula (II), and c) reacting the products from step a) or b) with a nucleophile identical to $R^2$ or comprising $R^2$.

2. The method according to claim 1, wherein in step a) a compound according to the following general formula (IIIb)

is used as compound (III), wherein B one of the nucleobases guanine, adenine, cytosine, thymine or uracil, and $R^3$ is H, OH or a protecting group.

3. The method according to claim 1, wherein aminomethyl polystyrene is used as a solid phase.

4. The method according to claim 1, wherein X, in case of multiple substituents X independently from each other, is selected from the group consisting of H, Me, OMe, $MeSO_2$, ketone, formyl, ester, COOH, $NO_2$ and halogen.

5. The method according to claim 1, wherein the nucleophile is selected from the group consisting of phosphate, pyrophosphate, glycosyl phosphate, nucleoside, nucleoside monophosphate, nucleoside diphosphate, nucleoside triphosphate, nucleoside analog, nucleoside monophosphate analog, nucleoside diphosphate analog, nucleoside triphosphate analog, α-deprotonated glycosyl, amines, amino acids, or salts thereof.

6. The method according to claim 5, wherein the nucleoside or nucleoside analog Nucl in compound (II) and the nucleophile nucleoside or nucleophile nucleoside analog are the same or different.

7. The method according to claim 1, characterized by the further step of d) releasing the linker (L) from the residue $R^1$.

8. The method according to claim 1, wherein the method is carried out under inert gas atmosphere.

9. A compound of the general formula (IIIa)

wherein the compound (IIIa) may be substituted one or more times with X,

X is an electron acceptor, $R^1$ is ONucl or Nucl, wherein Nucl stands for a nucleoside selected from the group consisting of adenosine, guanosine, cytidine, thymidine, uridine, deoxyadenosine, deoxyguanosine, deoxycytidine, deoxyuridine, and deoxythymidine, or an analog thereof, n is 2, and $R^5$ and $R^6$ are, each H and wherein the succinyl residue —OOC—$(CH_2)_2$—COOH is covalently bound to an OH group of the sugar component of the nucleoside of $R^1$ or to a component analogous to a sugar component of the nucleoside analog of $R^1$.

10. The compound according to claim 9, being a compound of the general formula (IIIb)

wherein

B is one of the nucleobases guanine, adenine, cytosine, thymine or uracil, and $R^3$ is H, OH or a protecting group.

11. The compound according to claim 9, wherein X, in case of multiple substituents X independently from each other, is selected from the group consisting of H, Me, OMe, $MeSO_2$, ketone, formyl, ester, COOH, $NO_2$ and halogen.

* * * * *